US006723510B2

(12) United States Patent
Lubenow et al.

(10) Patent No.: US 6,723,510 B2
(45) Date of Patent: Apr. 20, 2004

(54) METHODS FOR SEPARATING PARTICULATE SUBSTRATES FROM SOLUTION WHILE MINIMIZING PARTICLE LOSS

(75) Inventors: Helge Lubenow, Köln (DE); Kerstin Steinert, Langenfeld (DE); Roland Fabis, Haan (DE); Joachim Ribbe, Düsseldorf (DE); Melanie Emmerlich, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/812,541

(22) Filed: Mar. 20, 2001

(65) Prior Publication Data

US 2001/0014466 A1 Aug. 16, 2001

Related U.S. Application Data

(63) Continuation of application No. 09/353,407, filed on Jul. 15, 1999.

(51) Int. Cl.[7] .......................... C12Q 1/68; C12N 15/00; C12N 15/63; C12N 1/20; C12N 21/04
(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2; 536/24.3, 23.1, 24.32, 24.33; 935/6; 436/518; 501/137; 523/201; 530/330

(56) References Cited

U.S. PATENT DOCUMENTS

| 4,009,213 A | * | 2/1977 | Stein et al. ............. 260/643 D |
| 4,877,830 A | | 10/1989 | Döbeli et al. .............. 525/54.3 |
| 4,888,367 A | * | 12/1989 | Quigley ........................ 524/17 |
| 5,047,513 A | | 9/1991 | Döbeli et al. ................ 530/412 |
| 5,128,103 A | | 7/1992 | Wang et al. ................... 422/64 |
| 5,147,529 A | | 9/1992 | Lee et al. .................... 210/695 |
| 5,284,933 A | * | 2/1994 | Dobeli ........................ 530/350 |
| 5,385,959 A | * | 1/1995 | Tsaur et al. ................. 523/201 |
| 5,439,829 A | | 8/1995 | Anderson et al. ........... 436/518 |
| 5,458,785 A | | 10/1995 | Howe et al. ................ 210/695 |
| 5,466,577 A | * | 11/1995 | Weisburg ........................ 435/6 |
| 5,646,016 A | | 7/1997 | McCoy et al. ............. 435/69.7 |
| 5,798,442 A | * | 8/1998 | Gallant et al. .............. 530/330 |
| 5,942,391 A | * | 8/1999 | Zhang et al. .................... 435/6 |
| 6,180,548 B1 | * | 1/2001 | Taoda et al. ................. 501/137 |
| 6,348,318 B1 | * | 2/2002 | Valkirs ....................... 435/7.1 |

FOREIGN PATENT DOCUMENTS

| EP | 0 691 541 A2 | 1/1996 |
| WO | WO 96/31781 | 10/1996 |
| WO | WO 97/31105 | 8/1997 |
| WO | WO 97/44671 | 11/1997 |

OTHER PUBLICATIONS

Helenius et al., "Properties of Detergents" *In Methods in Enzymology*, vol. 56, pp. 734–739 (Academic Press, Inc., New York, 1979).
Hochuli et al., *Bio/Technology*, 6:1321–1325 (1988).
Lönnerdal et al., *J. Appl. Biochem.*, 4:203–208 (1982).
Neugebauer, Judith M., "Detergents: An Overview", *In Methods in Enzymology*, vol. 182, pp. 239–253 (Academic Press, Inc., New York, 1990).
*Ni–NTA Magnetic Agarose Beads Handbook*, (Qiagen, Hilden, Germany, printed Jun. 1998, distributed Aug. 1998).
Porath et al., *Nature*, 258:598–599 (1975).
Sulkowski, *Trends in Biotechnology*, 3:1–7 (1985).

\* cited by examiner

*Primary Examiner*—Jeffrey Fredman
*Assistant Examiner*—Arun Chakrabarti
(74) *Attorney, Agent, or Firm*—Yankwich & Associates; Leon R. Yankwich; Thomas R. Berka

(57) ABSTRACT

The present invention provides a method for separation of a particulate matrix from a solution while reducing loss of particles during separation steps. Methods are also disclosed for isolation of molecules of interest using affinity particles or beads, wherein at least one step of the isolation is conducted in the presence of a detergent. The presence of detergent reduces the loss of matrix particles and enhances reproducibility and yield of the molecule of interest. The invention makes possible the manual and automated processing of affinity beads, especially magnetic beads, in multi-well as well as single-well vessels with significantly reduced bead loss, as compared with similar processes conducted in the absence of detergent.

46 Claims, 1 Drawing Sheet

METHODS FOR SEPARATING PARTICULATE SUBSTRATES FROM SOLUTION WHILE MINIMIZING PARTICLE LOSS

CROSS REFERENCE TO RELATED APPLICATIONS

This application is a continuation of U.S. application Ser. No. 09/353,407, filed Jul. 15, 1999.

FIELD OF THE INVENTION

The present invention provides a method for isolation and assay of molecules of interest using affinity matrices in the presence of detergent. These isolation methods have application in various fields of biology such as protein purification, nucleic acid purification, high throughput assays, diagnostic assays, functional genomics, functional proteomics, phage display, and protein expression profiling.

BACKGROUND OF THE INVENTION

Affinity separation techniques are increasingly used for the isolation or quantification of biological molecules. Chromatographic techniques that use magnetically attractable affinity particles or beads for separation of specific molecules from a liquid are well documented in biochemical, biomedical, and molecular biological research. Affinity separation techniques involve the suspension of finely divided affinity matrix particles in a solution that contains molecules of interest in an impure or dilute form. The molecules of interest are captured or immobilized on the matrix particles by virtue of specific or non-specific interactions between the molecules and an affinity ligand for such molecules associated with the surface of the affinity particles. The affinity particles and the bound target molecules of interest may then be separated or collected together using a variety of standard techniques, such as filtration, centrifugation, decanting, and the like.

Particularly useful materials and techniques, especially for automated separation processes, utilize magnetically attractable affinity beads. After binding the target molecule, application of a magnetic field to the vessel containing the magnetic affinity particles (beads) will cause them to migrate towards the source of the field, thus collecting and concentrating the beads at the wall of the vessel. With the magnetic field still applied, the remainder of the solution and unbound components (the supernatant) can be removed by pouring it off or by using a pipetting device, leaving the magnetically collected pellet of magnetic particles intact. Additional solution(s) can then be added and the magnetic field removed, thus allowing the beads to be resuspended. If the interaction between the magnetic affinity beads and the molecules of interest is disrupted (target molecule eluted), the molecules can be recovered by reapplying the field and removing and retaining the supernatant containing the purified/concentrated molecules of interest. If the affinity beads are being used in an assay, e.g., where only the presence of the target molecule needs to be determined or quantified, elution from the affinity matrix is not necessary and the beads having bound molecules of interest may be exposed to a detection reagent, such as a labeled antibody, enzyme, or the like.

Manual handling of affinity beads limits the possible throughput, and to increase throughput several automated and semi-automated technologies have been devised, for both single-sample and multi-sample vessels. Magnetic affinity beads, as mentioned above, lend themselves readily to such automated and semi-automated technologies, and practitioners are able to achieve a higher throughput by better separation of the magnetic beads and by increasing the number of samples processed per run. Processing can be increased by either moving the magnetic source in relation to the vessels (see, WO 96/31781) or by moving the vessel in relation to a single or multiple magnetic sources (see, U.S. Pat. Nos. 5,128,103 and 5,147,529). The throughput in certain instances has been increased by placing the magnetic source adjacent to the pipette tips containing the magnetic beads (see, WO 97/44671, WO 97/31105, and EP 0 691 541), or removing the liquid from the magnetic beads using an automated pipetting system (see, U.S. Pat. No. 5,458,785).

Many suitable affinity ligands are known for use in preparing affinity matrix particles capable of binding a molecule of interest. One class of ligands that has been used successfully in affinity separations is metal chelate linkers. Porath et al. introduced the use of metal chelate affinity chromatography for protein isolation in 1975 (see, Porath et al., *Nature,* 258:598–599 (1975)). This technology has since been used successfully in many types of separations (see, review articles, e.g., Lonnerdal et al., *J. Appl. Biochem.,* 4:203–208 (1982) and Sulkowski, *Trends in Biotechnology,* 3:1–7 (1985)). Metal chelate affinity separation is based on the discovery that metal ions, such as nickel, copper, and zinc, bound to or immobilized on a solid substrate or matrix, such as agarose or silica gels, can take part in a reversible interaction with electron donor groups situated on the surface of proteins, especially the imidazole side chains of histidine. At a pH value at which the electron donor group is present at least partially in non-protonized form, the protein is bound to the chromatography gel and can subsequently be eluted by means of a buffer with a lower pH value, at which the electron donor group is protonized. Nitrilotriacetic acid (NTA), bound to the carrier matrix via a spacer, has been very reliable as the chelate donor (see, e.g., U.S. Pat. No. 5,047,513).

Regardless of the type of ligand used to capture the molecule of interest, affinity separation techniques suffer from a common problem of bead loss during the separation process. This problem has been observed during automated as well as manual bead handling each time the affinity beads are washed, molecules are eluted from the beads, or supernatant liquids are removed or retrieved. If the beads are collected at the bottom of a vessel, such as a microtiter plate, there is a high risk that while removing solution, some beads will also be removed. The loss or removal of beads leads to irreproducible results, inaccurate quantitation of bound materials, lower yields in purification protocols, and a lower throughput in assays.

Unexpectedly, it has now been shown that the use of small amounts of detergents in conjunction with use of the affinity beads, the loss of beads can be significantly reduced. The invention described herein makes possible the manual and automatic processing of affinity beads, especially magnetic beads, in multi-well and single well vessels. Commercially available multi-well and/or single well formats (e.g., microtiter plates) and robots (e.g., BioRobot) may be used.

The present invention provides separation methods that are highly flexible and which are characterized by high sample throughput without risk of sample mix-up. These and other aspects and advantages of the invention will be apparent from the description and examples presented below.

SUMMARY OF THE INVENTION

The invention provides methods for separating a finely divided particulate matrix from a solution so as to minimize loss of particles or beads from the matrix. More particularly, the present invention provides methods of isolating molecules of interest from a sample or solution using affinity particles or beads. The methods described herein provide the means for reducing loss of affinity particles or beads during a separation process, for increasing yields of target molecules of interest, and for increasing the accuracy and reproducibility of assay methods based on affinity separations.

In its broadest aspects, the present invention relates to a method of separating particles from a solution comprising the steps:
(a) combining a solution with a finely divided particulate matrix, in the presence of detergent;
(b) collecting the particles of the particulate matrix, e.g., by centrifugation, filtration, magnetic force (if the particles are magnetically attractable), etc.;
(c) removing supernatant solution.

Where the particles are affinity particles, the present invention provides a method for isolating a molecule of interest from a solution in a vessel, comprising the steps of:
(a) contacting the solution with affinity particles insoluble in the solution and capable of binding with said molecule of interest, in the presence of detergent; and
(b) separating the affinity particles from the rest of the solution, e.g., by introducing a magnetic field across the vessel (for magnetic affinity beads), centrifugation, filtration, etc.

Alternatively, the affinity particles may be treated with detergent prior to the contacting step.

The affinity particles and bound molecules of interest may be subjected to additional steps, depending on the object of the separation (i.e., whether the molecule of interest is being assayed, detected, recovered, or purified from the solution). Such additional steps include washing steps, e.g., in which the separated particles are resuspended in another solution; elution steps, in which the separated particles are subjected to solution conditions causing disruption of the affinity interaction between the particles and the molecules of interest, causing the molecules to be released from the particles; assay or detection steps, wherein the separated particles are contacted with detection reagents, such as labeled monoclonal antibodies specific for the bound molecule of interest.

In a particular embodiment of the invention, a magnetic separation method comprises:
(a) contacting a solution with magnetic particles in a vessel, in the presence of detergent;
(b) bringing the vessel and a magnet into proximity with each other, whereby said magnetic particles are immobilized within the vessel (i.e., by magnetic force);
(c) removing supernatant from the vessel;
(d) adding new solution to the vessel; and
(e) separating the vessel and the magnet and re-suspending the particles in the new solution.

In the foregoing embodiment, it will be recognized that steps (d) and (e) may be reversed, to the same effect.

The methods according to the present invention may be applied to the separation of a variety of molecules from various solutions. For example, molecules of interest may be peptides, polypeptides, proteins, nucleotides, nucleic acids, carbohydrates, lipids, complexes or organic molecules. Preferably, the methods of the present invention are used to isolate proteins and nucleic acids. More preferably, the methods are used to isolate 6x-His-tagged proteins.

Magnetic particles useful in preferred methods of the present invention may be any of a variety of materials including, for example, ferromagnetic beads, superparamagnetic beads, and combinations thereof. The particulate matrix materials that are advantageously separated according to the methods of the present invention may be any solid substrate materials insoluble in the solution(s) in which they are suspended. Typical examples include particulate agarose, silica, nitrocellulose, cellulose, acrylamide, latex, polystyrene, polyacrylate, polymethacrylate, polyethylene polymers such as polyvinyl alcohol, glass particles, silicates such as calcium, magnesium and aluminum silicates, metal oxides such as titanium oxides, tin oxides, etc., apatites, and the like, and combinations thereof.

The detergents used in the methods of the present invention are nonionic, anionic, zwitterionic, and cationic detergents, and combinations thereof. Preferably, the concentration of detergent used in the methods of the invention is at least about 0.0005–2.0% (v/v). In a preferred embodiment, the detergent is a nonionic detergent selected from a group consisting of Tween 20, Triton X-100, Nonidet P-40, and combinations thereof. In another embodiment of the invention, the detergent is the cationic detergent dodecyltrimethyl ammonium chloride. In another embodiment of the present invention, the detergent is an anionic detergent selected from a group consisting of sodium dodecyl sulfate (SDS), sarkosyl, and combinations thereof. In another embodiment of the invention, the detergent is the zwitterionic detergent CHAPS.

According to the methods of the present invention, the concentration of detergent should not exceed about 2% (v/v). Preferably, the concentration of a nonionic detergent according to the methods of the present invention is at least about 0.005% (v/v). Preferably, the concentration of an anionic detergent according to the methods of the present invention is at least about 0.05% (v/v) and does not exceed about 1% (v/v). Preferably, the concentration of a cationic detergent according to the methods of the present invention is at least about 0.5% (v/v) and does not exceed about 1% (v/v). Preferably, the concentration of a zwitterionic detergent according to the methods of the present invention is at least about 0.01% (v/v) and does not exceed about 2% (v/v).

Most preferably, the nonionic detergent Tween 20 is used at a concentration of at least about 0.05% (v/v) in the methods of the present invention when used in the isolation of nucleic acids or proteins.

This invention provides, in an affinity system, an improvement in signal, signal to noise ratio, reproducibility, and yield, by adding a small amount of detergent to the solution or treating the matrix particles or beads with a small amount of detergent.

DESCRIPTION OF THE DRAWING

FIG. 1A illustrates binding of a molecule of interest (6) to an affinity ligand (4) immobilized on a bead (2) of a matrix material.

FIG. 1B illustrates a two-step capture of a binding partner (12) for an interacting molecule (6), which has been immobilized on a matrix bead (2) by binding to or complexing with affinity ligand (8), e.g., as where a chelated metal (8) on a matrix bead (2) binds a histidine tag (10) fused to a protein (6), which protein (6), in turn, is capable of binding to another protein (12).

FIG. 1C illustrates the use of affinity beads (2+4) capable of binding to a complex (13) of two binding partners (12 and 14) such as and antibody/antigen complex or a binding complex of a cell and a protein or small molecule reactive with a surface antigen.

DETAILED DESCRIPTION OF THE INVENTION

Figure 1:
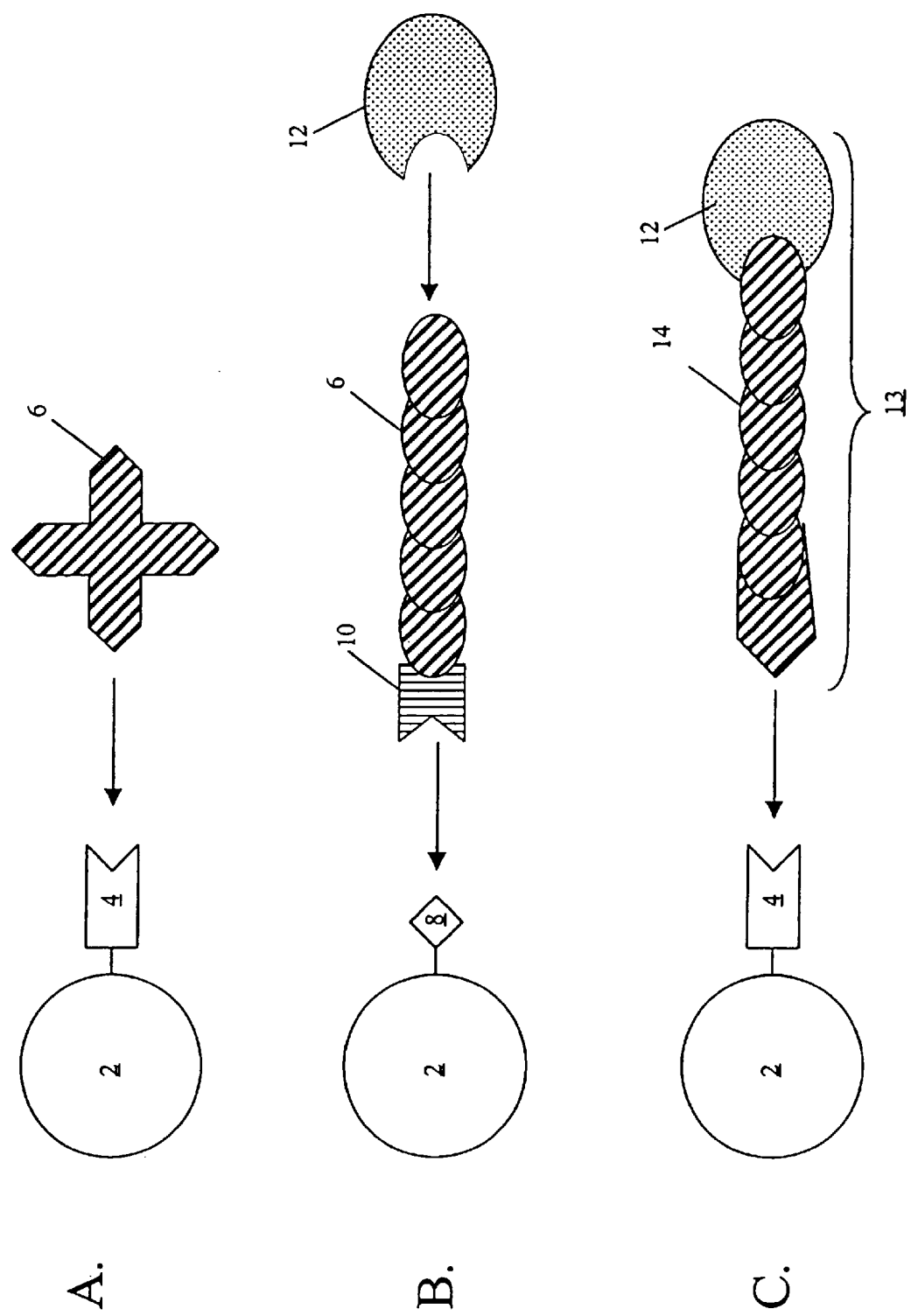
FIG. 1 is a schematic diagram illustrating particular types of affinity interactions and assays contemplated herein that may be improved in accordance with the methods of the present invention.

The present invention relates to methods for separating solid particles from a solution while minimizing loss of particles. The methods are especially useful for separations calling for isolation of molecules of interest using an affinity matrix of beads or particles, especially magnetic affinity beads or particles. In particular, the methods of the invention disclosed herein are based on the discovery that treating or exposing the beads with detergent improves the handling of the particles, and, with respect to isolation of a molecule of interest using affinity particles capable of binding the molecule of interest, improves the yield of such molecule isolated and improves the reproducibility of the separation. The use of such detergents also significantly reduces loss of particles in the course of separation processes, and for affinity separations increases signal and allows for higher signal to noise ratios.

In the following sections, the terms "sample" and "solution" are used to describe any preparation containing a molecule of interest or any medium in which the particles to be separated can be dispersed. The molecule of interest in a sample may be at any of a variety of states of purity, for example, less than 1% pure to greater than 90% pure. Useful samples and solutions will include crude cell lysates or biological fluids retrieved or extracted from humans or other animals, plants, bacteria, or viruses, and which may contain a molecule of interest.

The term "vessel" is used to describe a support, well, plate, tube, slide, filter, container, or dish which holds the sample or solution during purification or isolation procedures described herein.

The term "affinity particle" is used to describe any particle bearing an affinity ligand that is capable of binding (forming an affinity complex) with a molecule of interest. Any affinity ligand may be used that exhibits an acceptable affinity and specificity for the molecule of interest under the conditions of the contacting step. Such affinity ligands for use on particulate matrices include, without limitation, antibodies for a particular antigen, antigens for a particular antibody, antibodies recognizing a class of molecules such as a class of IgG molecules (e.g., anti-human IgG, anti-mouse IgG), streptavidin (or streptavidin-tagged fusion proteins) for binding biotin or biotin-tagged fusion proteins, glutathione for binding GST, cellulose for binding CBD, amylose for binding MBP, ion exchange resins, hydrophobic interaction resins, oligo-dT for binding poly A tail of mRNA, nucleic acid polynucleotides for binding complementary polynucleotides, ligands for binding cells (i.e., binding molecules for cell-surface markers), phage ligands, antibodies recognizing cell or phage surface antigens, and any other type of polypeptide, nucleotide or small molecule capable of affinity interactions with a binding partner, whether another protein, DNA, RNA, or small molecule. Specific mention is made of metal chelate affinity particles, in particular nickel ion chelate materials, such as nickel-nitrilotriacetic acid (Ni-NTA) coated agarose beads.

The term "matrix material" is used to describe any of a variety of solid materials dispersible in a sample or solution. Such materials are well known and include, for example, agarose, silica, nitrocellulose, cellulose, acrylamide, latex, polystyrene, polyacrylate, polymethacrylate, polyethylene polymers such as polyvinyl alcohol, glass particles, silicates such as calcium, magnesium and aluminum silicates, metal oxides such as titanium oxides, tin oxides, etc., apatites, and the like, and combinations thereof. Such materials are typically in the form of finely divided powders wherein the materials are in the form of small particles or beads, such that suspension in solution forms a matrix of particles which at sufficient concentration takes on the consistency of a resin or gel. Particulate materials capable of binding a molecule of interest in solution are referred to as "affinity particles" or an "affinity matrix". Matrix materials can be magnetic. The term "magnetic matrix material" is used to describe a matrix material that contains metal particles which are attracted to a magnetic field. The magnetically attractable metal or metal oxide particles are embedded throughout or at the core of the matrix particles. Unless noted otherwise, the term "particles" and "beads" are used interchangeably in describing the matrix materials useful in the methods of the invention.

The term "introducing a magnetic field" is used to describe any mechanism whereby a magnetic force is applied to attract or collect the magnetic matrix particles. The magnetic field may be introduced by any number of methods including, but not limited to, automated methods that introduce a single or multiple magnets at various locations of a vessel containing the magnetic particles to collect or temporarily immobilize the magnetic particles, or manual localization of a magnet to achieve the same result.

The term "His-tagged protein", "6x-His-tagged protein", or "polyHis-tagged protein" is used to describe a fusion protein in which a protein of interest is fused to a metal chelating group which is a polypeptide segment comprised of a plurality of histidine residues or other chelating amino acids such as cysteine, arginine, or serine, most preferably a segment completely comprised of histidine residues. Preferably the plurality of histidine residues is at least two or more, most preferably six such residues, forming a "6x-His-tagged" protein. Fusion proteins containing an affinity peptide tag are easily purified from samples including cultures of recombinant eucaryotic and prokaryotic organisms transformed to produce such fusion proteins. The fusion proteins containing an affinity peptide can also be used to assay for a molecule of interest. The affinity of a polyHis tag for copper, nickel, cobalt, or zinc allows the fusion product to be quickly separated from the bulk of other bacterial proteins with up to 95% purity using metal chelate affinity chromatography (Hochuli et al., *Bio/Technology*, 6: 1321–1325 (1988)). This affinity also allows efficient capturing of a molecule of interest and assaying for its presence in a known or unknown sample. The fusion protein also allows for binding studies, and capture assays. Other affinity tags may also be used and are discussed below.

In the present invention, detergent may be added throughout the methods described herein to enhance separation and collection of particulate substrates. In preferred embodiments of the invention, a detergent is present at the binding step when the sample and the affinity particles are combined, that is, when the molecule of interest is first contacted with the affinity matrix (see, Examples 1–3). The detergent may be added to the sample prior to the addition of the affinity particles. Alternatively, the detergent may be introduced after the affinity particles and the sample are initially mixed or brought into contact with each other (see, Example 4). Affinity beads may also be suspended in an aqueous solution or buffer containing detergent and then combined with a sample containing a molecule of interest. The beads may also be incubated with a detergent, washed, stored, and used later, while still realizing the benefits of the present invention. Preferably, the beads are exposed to detergent after binding to a molecule of interest has taken place but before the beads are collected or concentrated.

While not wishing to be bound by any particular scientific theory, the affinity beads, when exposed to detergent as described herein, are able to form more compact aggregates or pellets when collected or concentrated, e.g., by centrifugation or the application of a magnetic field (where magnetic beads are used). It appears that the presence of detergent used in the purification process changes the charge characteristics of the matrix material, so that a more compact arrangement of matrix particles or beads is formed during collection. The compact arrangement allows for more efficient removal of unbound molecules and, hence, more efficient washing or elution of the molecule of interest. The enhanced packing of the affinity beads during collection decreases bead loss during handling and thereby improves the yield of bound molecules and improves the reliability and consistency of measurements or assays using the beads.

Care should be taken that the detergent concentration does not significantly interfere with the binding of the molecule of interest to the affinity particles. In order to avoid such interference during the binding phase of a separation procedure, the detergent may be omitted from this binding step and introduced during the wash or elution steps of the method. It should be kept in mind, however, that any collection or wash steps conducted before the introduction of detergent in accordance with the invention will be characterized by (avoidable) bead loss and decreased yield and accuracy.

The methods of this invention are particularly useful where the affinity matrix is in the form of magnetically attractable particles or "magnetic beads", as they are commonly referred to in the art.

The presence of detergent is the critical element of the methods of the present invention. The detergent can be present in the methods of the present invention either throughout the entire procedure, or it may be added when the sample is contacted with the affinity particles. Once the beads have been treated with the detergent, all subsequent steps in the procedure can be performed with or without detergent without any significant influence on yield or reproducibility as a result of bead loss (see, Example 6).

When the detergent is added to the sample at the onset of the procedure, care must be taken so that the concentration of the detergent does not interfere with the interaction of the molecule of interest and the matrix bead. Preferably, the concentration of the detergent in the separation methods described herein is in the range of from about 0.0005% to 2.0% (v/v).

Detergents form one class of polar lipids, characterized by their solubility in water. They have a bipartite structure with one hydrophobic portion and one hydrophilic portion. The presence of these two groups not only makes detergents useful in lysis of lipid membranes, solubilization of antigens, and washing of immune complexes, but it also may change the charge characteristics of materials in a sample, such as, in preferred embodiments herein, the charge characteristic of magnetic affinity particles. A wide variety of chemicals can be characterized as detergents and may be used in the methods of the present invention. Most detergents have hydrophobic regions with a 6- to 16-member alkyl chain (either with or without a phenolic moiety) or a structure that resembles the aromatic hydrophobic moiety of bile salts. The hydrophobic region of many detergents can disrupt lipid bilayers and cell membranes, leading to dissolution of the bilayer or membrane components. Such detergents are particularly useful in a variety of biochemical protocols, including methods described herein.

Detergents are also classified based on the type of hydrophilic group(s) present in a detergent molecule. These groups can be anionic, cationic, amphoteric, nonionic, and zwitterionic. In general, nonionic detergents (e.g., Tween 20 and Triton X-100) and zwitterionic detergents (e.g., CHAPS) are less denaturing to proteins than ionic detergents (e.g., SDS). Of the ionic detergents, sodium cholate and sodium deoxycholate are less denaturing than other ionic detergents.

Many properties of detergents can be described by three values: the critical micelle concentration (CMC), the micelle molecular weight (MMW), and the hydrophile-lipophile balance (HLB). The CMC is the concentration at which monomeric detergent molecules join to form micelles. Below this concentration, detergent molecules are found predominantly as monomers which may bind to or disrupt hydrophobic molecules without dissolving the hydrophobic molecules in aqueous solutions. Above the CMC, the detergent molecules form micelles which are effective at dissolving hydrophobic molecules in aqueous solutions. The MMW is the molecular weight of a micelle formed by a particular detergent. Detergents with large MMWs, such as the nonionic detergents, may be difficult to remove by dialysis. However, an advantage to using some nonionic detergents is the ability to dissolve molecules in a non-denatured state which retains important functional properties of the molecules. The HLB gives a numerical value to the overall hydrophilic properties of the detergent. Values above 7 indicate that the detergent is more soluble in water than oils. For most biological and biochemical protocols, HLB values of 12.5 and higher are needed. Although there are exceptions, the HLB values can be used to give a general view of how denaturing a detergent will be towards biomolecules, especially proteins. Values between 12 and 16 are relatively nondenaturing, while values above 20 indicate increasing denaturing characteristic. However, this correlation does not always apply and will differ from one protein to another. Both the CMC and MMW will vary in different buffers. In general, adding salts will lower the CMC and raise the micelle size. The addition of as little as 100 mM NaCl may induce dramatic changes in these values. The extent of change in CMC or MMW caused by varying the temperature or pH will also vary depending on the detergent. Two detergents that are drastically affected by temperature and pH are sodium dodecylsulfate (SDS) (temperature below 20° C. will often lead to crystallization) and sodium deoxycholate (DOC) (insoluble below about pH 7.5).

The detergents that may be used in the methods of the present invention can be selected from any of anionic, cationic, nonionic, or zwitterionic detergents and combinations thereof. Anionic detergents useful in the present invention include, but are not limited to, sodium dodecylsulfate (SDS), sodium dodecyl-N-sarcosinate, sodium cholate, sodium deoxycholate. Cationic detergents useful in the present invention include, but are not limited to, dodecyltrimethyl ammonium chloride, cetyltrimethylammonium bromide (CTAB). The zwitterionic detergents useful in the methods described herein include, but are not limited to, 3-[(cholamidopropyl)-dimethyl-ammonio]-1-propanesulfonate (CHAPS), BigCHAPS, CHAPSO, DDMAU, N-dodecyl-N,N-dimethylglycine, lauryldimethylamine oxide (LADAO, LDAO), and 3-dodecyl-dimethylammonio-propane-1-sufonate. Nonionic detergents useful in the present invention include, but are not limited to, polyoxyethylene (10) cetyl alcohol (e.g., Brij 56™, ICI Americas Inc.); polyoxyethylene (20) cetyl alcohol (e.g., Brij 58™, ICI, Americas Inc.); polyoxyethylene (23) lauryl alcohol (e.g., Brij 35™, ICI Americas Inc.); polyoxyethylene (4-5) p-t-octyl phenol (Triton X-45); polyoxyethylene (7-8) p-t-octyl phenol (Triton X-114); polyoxyethylene (9) p-t-octyl phenol (Nonidet P-40); polyoxyethylene (9-10) p-t-octyl phenol (Triton X-100); polyoxyethylene (9-10) nonylphenol (Triton N-101); polyoxyethylene (20) sorbitol monolaurate (e.g., Tween 20™, ICI Americas Inc.); polyoxyethylene (20) sorbitol monopalmitate (e.g., Tween 40™, ICI Americas Inc.); polyoxyethylene (20) sorbitol monooleate (e.g., Tween 80™, ICI Americas Inc.); octyl-β-glucoside; APO-10; APO-12; cyclohexyl-n-ethyl-β-D-maltoside; cyclohexyl-n-hexyl-β-D-maltoside; cyclohexyl-n-methyl-β-D-maltoside; n-decanoylsucrose; n-decyl-β-D-glucopyranoside; n-decyl-β-maltopyranoside; n-decylβ-D-thiomaltoside; n-dodecanoyl sucrose; and heptane-1,2,3-triol; and the like. Most preferably, nonionic detergents such as Tween 20, Triton X-100, and Nonidet P-40 are used in the methods of the present invention. Methods of the invention which incorporate such nonionic detergents are particularly effective at reducing loss of affinity particles or beads during various manipulations (e.g., bead collection, washes, elution), increasing yields of molecules of interest which are isolated using particulate affinity matrices, increasing reproducibility (lowering variance) of results, increasing the signal achieved in an assay, increasing signal to noise ratio, and increasing the signal resulting from the binding of the molecule of interest in a capture assay.

The methods of the present invention are readily adaptable to widely used sample vessels such as multi-well plates. These multi-well systems are particularly well suited for use in semi- or fully-automated assay systems that are available commercially. A number of different automated systems are available and could be used with the present invention. For example, PCT publication WO 96/31781 describes an automated system that handles magnetic beads, and which processes up to 16 specially designed sample vessels. The magnet is moved in relation to the tubes at the different stages of the assay process to facilitate the binding, wash, and elution steps of the assay. U.S. Pat. Nos. 5,128,103 and 5,147,529 also describe an automated system in which single sample tubes are automatically guided past one or more magnets to retrieve beads containing bound molecules of interest. Patent publications WO 97/44671, WO 97/31105, and EP 0 691 541 describe robots or devices in which magnetic beads are separated from liquid inside a pipette tip by the positioning of an external magnet adjacent to the tip. This allows processing of up to 24 samples simultaneously. A magnet construction is described in U.S. Pat. No. 5,458,785 that allows the removal of liquids from the magnetic beads by automatic pipetting. This system has a ring-shaped magnet that surrounds the sample vessel and a second magnet, which is positioned at the base of the sample vessel. Positioning the sample vessel on one of these magnets influences the form and density of the magnetic bead pellet, immobilizing the beads to permit the removal of liquids by pipetting without disturbing or entraining the beads. However, this magnet system is not suitable for multi-well plates.

The present invention enhances the use of multi- and single-well procedures because the presence of detergent at various stages of the isolation scheme allows for better separation of magnetic beads or particles from the well walls and a more efficient collection of all the beads towards the source of the magnetic field. Better separation and collection of beads enhances the yield of the molecule of interest that becomes bound to the magnetic affinity beads and the reproducibility of the assays in the aforementioned automated systems. Accordingly, these methods also reduce the number of times a procedure needs to be carried out to isolate or detect a molecule of interest in a sample(s). The present invention can be applied to the purification or isolation scheme of a variety of molecules including, but not limited to, peptides, polypeptides, proteins, nucleotides, nucleic acids (polynucleotides), carbohydrates, lipids, and organic molecules, including synthesized organic molecules, or any type of molecule or molecule complex separable by affinity interactions with an appropraite substrate.

Affinity beads for use in accordance with the present invention will be characterized by a surface affinity ligand for a molecule of interest. Any affinity ligand may be used that exhibits an acceptable affinity and specificity for the molecule of interest under the conditions of the contacting step. Many types of affinity ligands are known, and suitable affinity ligands for use on particulate matrices in the present invention include, without limitation, antibodies for a particular antigen, antigens for a particular antibody, antibodies recognizing a class of molecules such as a class of IgG molecules (e.g., anti-human IgG, anti-mouse IgG), streptavidin (or streptavidin-tagged fusion proteins) for binding biotin or biotin-tagged fusion proteins, glutathione for binding GST, cellulose for binding CBD, amylose for binding MBP, ion exchange resins, hydrophobic interaction resins, oligo-dT for binding poly A tail of mRNA, nucleic acid polynucleotides for binding complementary polynucleotides, ligands for binding cells (i.e., binding molecules for cell-surface markers), phage ligands, antibodies recognizing cell or phage surface antigens, and any other type of polypeptide or complex (see, FIG. 1 and discussion, infra) capable of affinity interactions with a binding partner, whether another protein, DNA, RNA, or small molecule. Specific mention is made of metal chelate affinity ligands, in particular nickel ion chelate materials, such as nickel-nitrilotriacetic acid (Ni-NTA) coated particles. Ni-NTA-coated magnetic agarose beads are particularly preferred for isolation of His-tagged molecules of interest.

The methods of the present invention are particularly useful for making separations based on protein/protein interactions. The target molecule of interst can either be known or unknown: Affinity separation applications are becoming particularly important in assessing unknown proteins and deciphering their function in proteomics, e.g., where a large amount of genetic material is processed and determining the functionality of the encoded proteins is essential.

The types of separations for which the discovery of the present invention will be used include, without limitation, assay and/or purification methods, purification and/or capture assays, capture or affinity immobilization of a molecule of interest, detection of a molecule of interest, purification (i.e., isolation, elution and recovery) of a molecule of interest, etc. FIG. 1 illustrates typical separations that are contemplated: For example, in FIG. 1A, an affinity bead comprised of a particulate matrix material (2) coated with affinity ligands (4) may be used to bind or capture a molecule of interest (6), which may be any sort of binding parter (i.e., molecule, antigen, protein, polynucleotide, etc.) for the affinity ligand, as discussed above. After capture, the molecule of interest (6) may be detected on the affinity bead (2+4) or eluted from the affinity bead after separation from the original sample, using known procedures. In another type of affinity interaction contemplated, illustrated in FIG.

1B, an affinity bead comprised of matrix particles (2) and an affinity ligand (8) are used to immobilize a molecule of interest (6), e.g., a protein by means of a synthetic binding moiety (10) capable of reacting with the affinity ligand (8) on the bead. This affinity bead/immobilized molecule complex may be further employed to interact with another molecule (12), i.e., which is capable of binding to a molecule (6) or the affinity complex (2+8+10+6). For example, the affinity bead may comprise an agarose bead (2) with chelated metal ions (8), such as with a Ni-NTA agarose magnetic bead, and a protein of interest (6) may be captured on the affinity beads (2+8) by means of a 6x-His tag (10) fused to the protein (6), which tag (10) is reactive with the metal chelate (8) on the bead (2). After formation of this complex, the protein (6) may be used to capture another molecule capable of reacting with another portion of the protein. It is seen that this method can be used to capture then detect or elute the protein (6), to capture and then detect or elute the protein binding partner (12), to capture and then detect or elute the complex of the protein (6) and its binding partner (12), or to remove the protein (6) and/or the binding partner (12) from a solution to which the affinity beads are added. Finally, FIG. 1C illustrates the use of an affinity bead comprised of a bead (2) coated with an affinity ligand (4) to bind with a preformed complex (13) of binding partners (12 and 14). The complexes can be captured, then detected, eluted or removed, according to the desired use. In accordance with the present invention, treatment of the affinity beads (2, with 4, 8) with small amounts of detergent at some point in these processes before the beads are collected for separation from a solution or sample, leads to better handling of the beads (and whatever they may have complexed) and reduced loss of beads during separation and resuspension.

In detection methods, the molecule of interest may be observed using any sort of assay signal (e.g., chromogenic, fluorescent, radioactive, or enzymatic reaction).

In purification methods, the purification strategy may vary depending on whether a native form of a molecule or the denatured form of the molecule is being purified. Since the biochemical properties of the molecule of interest are dependent on the individual molecule, itself, and these properties can strongly affect binding to affinity particles, the exact procedure for purification of a particular form of a molecule will vary. In general, the purification of a molecule of interest will be improved by minimizing non-specific binding to affinity particles. For example, in the case of isolating a His-tagged protein, non-specific interactions will be minimized by using low concentrations of imidazole in the lysis/binding buffers used in the intial steps in the purification. The presence of imidazole at concentrations up to 20 mM effectively inhibits the binding of many contaminating proteins to the affinity particles without affecting the binding properties of the His-tagged protein of interest.

If a protein of interest is to be purified from cells, the cells containing the protein of interest may be lysed using sonication, or homogenization after treatment with lysozyme (for example at 1 mg/ml). Such procedures can be performed in cells cultured in multi-well plates such as, 96-well flat bottom plates. To inhibit protein degradation, cells and buffers are typically kept at 0° C.–4° C. at all times, and the addition of protease inhibitors may also be necessary. At native conditions all buffers should contain sufficient ionic strength to prevent non-specific interactions between proteins and magnetic affinity particles, if they are used. For example, typically, the minimum salt concentration during binding and washing steps should be about 300 mM NaCl and the maximum concentration should not exceed 2 M NaCl.

For denaturing conditions, cells are typically lysed in either 6M guanidine-hydrochloride (GuHCl) or 8M urea. It is preferable to lyse the cells in the milder denaturant, urea, so that the cell lysate can be analyzed directly on an SDS polyacrylamide gel. GuHCl is a more efficient solubilization and cell-lysis reagent, however, and may be preferable for solubilizing some proteins.

Binding may be carried out with samples under native or denaturing conditions. For some molecules of interest, separation may also be carried out without clearing the samples, but care should be taken that the sample is not too concentrated. For example, the volume of a crude, uncleared E. coli cell lysate sample should not be more than 1/5 or 1/10 of the culture volume (e.g., cells from 1 ml of culture are preferably lysed in 0.2 ml or at the very least 0.1 ml lysis buffer). Deoxyribonucleic acid (DNA), which can disturb the separation of the beads, can be eliminated by DNase treatment. Yield and purity of isolated proteins may be slightly reduced when uncleared lysates are used.

Washing and elution steps are contemplated where recovery of highly purified or concentrated target molecules is desired. However, for many applications wash and/or elution steps will not be necessary, as where the object of the isolation procedure is only detection of the presence or absence of a molecule, or where the object is to selectively remove a particular molecule of interest and obtain a sample (supernatant) substantially free of the molecule of interest. For such applications, the bound matrix/molecule complex may be assayed for the presence or absence of the molecule with any number of methods known in the art including, but not limited to, antibody detection of the complex or of the immobilized target molecule.

For applications where a washing step is employed, any suitable wash solution may be used. For example, for assays of physiological samples where magnetic affinity beads are used, the composition of a wash buffer may be 50 mM $NaH_2PO_4$, 300 mM NaCl, 20 mM imidazole, at pH 8.0. The composition of the wash buffer for separation under denaturing conditions may be 8 M urea, 0.1 M $NaH_2PO_4$, 0.01 M Tris-Cl, 0.05% Tween 20, pH 6.3.

Washing steps in a separation process where magnetically attractable affinity beads are used are accomplished first by applying a magnetic field (which immobilizes the beads (and any bound molecules of interest) against the wall of the vessel adjacent the magnetic field), and then by removing the unbound molecules and buffer (e.g., by pipetting or decanting), after which the magnetic beads are resuspended in a wash solution, in the absence of the magnetic field. The non-specific binding of unbound molecules to the magnetic beads may be inhibited by washing with buffers of slightly reduced pH or with buffers containing low concentration of imidazole. After resuspending the matrix beads in an appropriate wash solution, the magnetic field is re-introduced, and the matrix beads are collected at the source of the magnetic field. Separation of the beads from the supernatant in any of the aforementioned steps may be accomplished by inverting the vessel and pouring the supernatnat out (retaining the beads by magnet), or by manually, semi-automatically, or robotically suctioning or pipetting the supernatant from the vessel. The presence of the detergent in any separation step allows for better collection (immobilization) of the affinity beads and results in reduced bead loss. Wash steps may be repeated any number of times to separate contaminants or other non-specific and unbound molecules from the affinity beads.

Elution of the bound molecule of interest from affinity particles may be desirable in some separations. As with wash steps, an elution step may not be necessary in certain applications, such as when it is sufficient to simply immobilize the molecule of interest on the affinity matrix and detect its presence there. However, in applications that require the elution step, elution may be advantageously performed according to this invention, in the presence of a detergent, to allow for efficient separation of the matrix material from the eluted molecule of interest.

The composition of the elution buffer will vary depending on the molecule to be eluted. For example, the composition of the elution buffer used in separations under native conditions may be 50 mM $NaH_2PO_4$, 300 mM NaCl, 250 mM imidazole, at pH 8.0. However, the composition of the elution buffer for separation under denaturing conditions may be 8 M urea, 0.1 M $NaH_2PO_4$, 0.01 M Tris-Cl, 0.05% Tween 20, at pH 4.5. As a particular example, 6x-His-tagged proteins may be released from magnetic NTA-agarose beads either by competition with imidazole, or by reducing the pH. Monomers are generally released with imidazole concentrations greater than 100 mM or at approximately pH 5.9, whereas multimers are released with 200 mM imidazole or at around pH 4.5. Usually, elution buffers containing 250 mM imidazole (pH 8) or buffers at pH 4.5 (e.g., Buffer-E, Qiagen GmbH) are recommended.

In the case of 6x-His-tagged proteins, when purified by magnetic beads containing Ni-NTA linkers, 100 mM EDTA may also be used in the elution step. EDTA chelates nickel ions and removes them from the NTA groups. This causes all bound protein to elute as a protein-metal complex.

Additional embodiments and teachings of the invention are provided by the following non-limiting examples.

EXAMPLES

Example 1

Automated Purification of 6x-His-Tagged Thioredoxin Under Native Conditions Using Ni-NTA Coated Magnetic Agarose Beads This example demonstrates the positive effects of the addition of detergent on yield and uniformity in an automated protein purification procedure using ferromagnetic agarose beads under non-denaturing conditions.

E. coli M15 cells (80 ml aliquot), expressing a 6x-His-tagged recombinant thioredoxin fusion protein, were lysed in a lysis buffer (50 mM $NaH_2PO_4$, pH 8.0, 300 mM NaCl, 10 mM imidazole, 1 mg/ml lysozyme). The lysate was centrifuged to remove the un-lysed cells and cell debris, and the supernatant (cleared lysate) was aliquoted in 80 wells of a 96-well flat-bottom multi-well plate. A nonionic detergent, Tween 20 (Sigma Inc.), was added to 40 of the samples to an end concentration of 0.05% (v/v). In order to compare the effect of detergent on the yield of protein, all the buffers used throughout the procedure contained 0.05%(v/v) of Tween 20. The buffers used in the control wells contained no detergent throughout the procedure. All samples were placed on an automated pipetting system (e.g., BioRobot 9600, Qiagen GmbH), and all further pipetting steps were performed automatically. A 20 $\mu$l aliquot of a 5% (v/v) suspension of Ni-NTA coated magnetic agarose beads was added to each sample, and the mixtures were incubated for 1 hour at room temperature on a shaker platform at 750 rpm. During this step, the thioredoxin protein was bound specifically via its 6x-His (hexahistidine) tag to the Ni-NTA groups on the agarose beads. Following the binding, all unbound cell ingredients were removed by placing the multi-well plate on a magnetic separator for 96-well plates (e.g., 96-Well Magnet, Qiagen GmbH, 1999 Product Guide Cat. No. 36915), shaking at 300 rpm for 1 min. to complete bead separation, and removing the supernatant with the probes of the robot. Clear differences in the separation behavior of the magnetic beads could be observed by comparing the samples processed in the presence of Tween 20 and with no Tween 20. While beads suspended in buffers containing Tween 20 were collected in a compact pellet in the magnetic field near the surface of the liquid, beads in buffers without Tween separated in a diffuse pellet at the bottom of each well. The diffuse pellets in the bottom of the wells resulted in bead loss during the buffer removal step.

Subsequently, the multi-well plate was detached from the magnet. The beads were resuspended by the addition of 200 $\mu$l washing buffer (50 mM $NaH_2PO_4$, pH 8.0, 300 mM NaCl, 20 mM imidazole, with or without 0.05% Tween 20) to each well and shaking at 750 rpm for 2 min. Removal of the wash buffer was subsequently performed by placing the multi-well plate on a 96-well magnet, shaking at 300 rpm for 1 min. and aspirating the supernatant. The wash step was repeated a second time with a lower volume (100 $\mu$l) to facilitate resuspension of the magnetic beads in a low volume of elution buffer. A 60 $\mu$l aliquot of an elution buffer (50 mM $NaH_2PO_4$, pH 8.0, 300 mM NaCl, 250 mM imidazole, with or without 0.05% Tween 20) was added to the beads, and elution was performed by incubating the plate for 5 min. at room temperature on a shaker platform at 750 rpm. The eluted proteins were harvested by placing the multi-well plate on the 96-well magnet and shaking the plate for 2 min. at 300 rpm. The buffer containing the eluted protein was then transferred into a new multi-well plate. Protein content in the eluate of each well was measured by the Bradford method (BioRad, Inc.) The average yield and statistical values are given in Table 1.

TABLE 1

|  | samples containing nonionic detergent | samples without nonionic detergent |
|---|---|---|
| Amount of protein ($\mu$g) in 50 $\mu$l of eluate | 3.239 | 2.317 |
| standard deviation | 0.258 | 0.900 |
| Variance (CV-value) | 8.0 | 38.8 |

As shown in Table 1, samples without detergent yielded less protein than samples containing the detergent, due to the loss of magnetic beads with bound protein during the wash steps. Moreover, the variance between different wells was much higher in the absence of detergent because of irregular bead loss.

Example 2

Automated Purification of 6x-His-Tagged Thioredoxin Under Denaturing Conditions Using Ni-NTA Coated Magnetic Agarose Beads in the Presence of a Nonionic Detergent This example demonstrates that protein purification under denaturing conditions (8 M urea) in an automated procedure using magnetic agarose beads gives significantly better yields in the presence of a nonionic detergent.

Protein purification was carried out using the following buffer solutions: lysis buffer (8 M urea, 0.1 M $NaH_2PO_4$, 0.01 M Tris, pH 8.0), wash buffer (8 M urea, 0.1 M NaH$_2$PO$_4$, 0.01 M Tris, pH 6.3), and elution buffer (8 M urea, 0.1 M NaH$_2$PO$_4$, 0.01 M Tris, pH 4.5). *E. coli* M15 cells (80 ml aliquot), expressing a 6x-His-tagged recombinant thioredoxin fusion protein, were lysed in a lysis buffer (50 mM NaH2PO$_4$, pH 8.0, 300 mM NaCl, 10 mM imidazole, 1 mg/ml lysozyme). The lysate was centrifuged to remove the un-lysed cells and debris, and the supernatant (cleared lysate) was aliquoted in 80 wells of a 96-well flat-bottom multi-well plate. Half of the samples were supplied with 0.05% Tween 20 nonionic detergent, and half of the samples were assayed in the absence of detergent. The separation behavior of the magnetic beads showed similar characteristics to that observed under native conditions, but bead loss during the buffer removal steps was even higher. As a result, the majority of the wells containing no detergent lost all their beads.

Protein content in the eluate of each well was determined by the Bradford method. The average yield and statistical values are given in Table 2. Samples without the detergent yielded much less protein. In most instances no protein was detected in wells without detergent, due to the loss of the magnetic beads. The variance between different wells was also much higher in wells without detergent.

TABLE 2

|  | samples containing detergent | samples without detergent |
| --- | --- | --- |
| average value | 5.484 | 0.236 |
| standard deviation | 0.855 | 0.401 |
| CV-value | 15.6 | 170.0 |

Example 3

Automated Purification of 6x-His-Tagged Chloramphenicol-Acetyl Transferase Under Native Conditions Using Ni-NTA Coated Magnetic Silica Beads This example demonstrates the positive effects of the addition of detergent in an automated protein purification procedure using superparamagnetic silica beads.

Protein purification was performed as described in Example 1, with the exception that 20 µl of a 1.25% (w/v) suspension of Ni-NTA coated magnetic silica beads was used instead of agarose beads. A 40 ml aliquot of *E. coli* cells expressing a 6x-His-tagged recombinant chloramphenicol acetyl transferase fusion protein was lysed as described in Example 1, and the cleared lysate was used in the assay.

A clear distinction was observed in the separation behavior of the silica beads in buffers containing detergent (Tween 20) as compared to the beads in buffers without detergent. While in the presence of detergent the beads were collected in a compact pellet near the surface of the liquid, the beads in buffers without detergent separated in a diffuse pellet at the bottom of each well. Bead loss resulted during the buffer removal step. In some instances, the automated procedure led to complete loss of beads in wells containing no detergent.

Protein content in the eluate of each well was determined according to the Bradford method. The average yield and statistical values are given in Table 3. Samples without detergent (Tween 20) yielded less protein than samples containing detergent, due to the loss of magnetic beads during the buffer removal steps. Variance between different wells was significantly higher without detergent because of irregular bead loss.

TABLE 3

|  | samples containing detergent | samples without detergent |
| --- | --- | --- |
| average value | 2.052 | 1.922 |
| standard deviation | 0.382 | 0.530 |
| CV-value | 18.6 | 27.6 |

Example 4

Automated Immunoassay of 6x-His-Tagged Thioredoxin Using Ni-NTA Coated Magnetic Agarose Beads This example demonstrates the positive effects of the addition of detergent on the uniformity of an automated protein assay procedure using magnetic agarose beads.

Purified 6x-His-tagged thioredoxin was diluted to 50 ng per 200 µl in dilution buffer (50 mM NaH$_2$PO$_4$, pH 8.0, 300 mM NaCl, 20 mM imidazole). A 200 µl aliquot of the protein dilution was pipetted into 24 wells of a 96-well multi-well plate. As a negative control, 200 µl of the above buffer without thioredoxin was pipetted into 24 wells.

The multi-well plate was placed on the working platform of an automated pipetting system (e.g., BioRobot 9600, Qiagen GmbH) and 20 µl of a 5% (v/v) suspension of Ni-NTA-coated magnetic agarose beads were dispensed into each well. The plate was shaken at room temperature on a shaker platform for 45 min. at 750 rpm to allow the target His-tagged protein to bind to the beads. Following the binding step, 0.1% Tween 20 nonionic detergent was added to 12 wells of the plate. For all following steps, these wells were processed in the presence of 0.05% Tween 20 nonionic detergent, whereas the other 12 wells were handled without detergent during the whole process.

After incubation for additional 15 min., the plate was transferred to a magnetic separator for 96-well plates (e.g., 96-Well Magnet, Qiagen GmbH, 1999 Product Guide Cat. No. 36915), and shaken for 1 min. at 300 rpm to complete bead separation. Supernatants were aspirated, the plate was removed from the magnet, and the magnetic beads were resuspended by the addition of 200 µl to each well of a washing buffer (50 mM NaH$_2$PO$_4$, pH 8.0, 300 mM NaCl, 20 mM imidazole with or without 0.05% Tween 20) then shaking for 5 min. at 750 rpm. The wash buffer was removed as described above and the beads were resuspended in 200 µl 50 mM NaH$_2$PO$_4$, pH 8.0, 300 mM NaCl, 3% BSA containing a polyclonal antibody recognizing thioredoxin. As described previously, half of the wells on the plate were incubated with detergent; the other half were incubated in the absence of detergent. The plate was shaken at 750 rpm for an hour at room temperature to allow for the binding of the antibody to the immobilized thioredoxin. The buffer was removed as described above, and the beads were washed twice. Subsequently, 200 µl of a secondary antibody coupled to horseradish peroxydase was added in buffer containing 50 mM NaH$_2$PO$_4$, pH 8.0, 300 mM NaCl, 3% BSA with or without Tween. The plate was shaken at 750 rpm for an hour at room temperature. The beads were washed twice and the amount of immobilized peroxidase was determined by the addition of 200 µl color reagent (10 mg o-phenylene diamine in 25 ml sodium-phosphate buffer, pH 5.0, 25 µl H$_2$O$_2$). The plate was incubated for 10 minutes at room temperature and the optical density was read at 450 nm.

The separation behavior of the magnetic beads showed similar characteristics as observed in purification procedures, with a significant amount of bead loss during the buffer removal steps, specifically in the wells without any detergent. This bead loss resulted in lower signals and higher standard deviation between the wells that contained no detergent.

detergent, and dodecyltrimethyl ammonium chloride was tested as a cationic detergent. In all cases, with all detergents, the beads formed a compact pellet near the surface of the liquid after the plates were transferred to the magnet. In contrast, when no detergent was added, the beads separated in a diffuse pellet at the bottom of the wells. The results are set forth in Table 5:

TABLE 5

| detergent concentration | 1% | 0.5% | 0.1% | 0.05% | 0.01% | 0.005% | 0.0005% |
| --- | --- | --- | --- | --- | --- | --- | --- |
| nonionic detergents | | | | | | | |
| Tween 20 | c | c | c | c | c | c | c |
| Triton X-100 | c | c | c | c | c | n.d. | n.d. |
| Nonidet P-40 | c | c | c | c | c | n.d. | n.d. |
| anionic detergent | | | | | | | |
| sodium dodecyl sulfate | c | c | c | c | d | n.d. | n.d. |
| cationic detergent | | | | | | | |
| dodecyltrimethyl ammonium | c | c | d | d | d | n.d. | n.d. |
| zwitterionic detergent | | | | | | | |
| CHAPS | c | c | c | c | c | d | n.d. |
| controls | | | | | | | |
| NaCl | d | d | d | d | d | n.d. | n.d. |
| water | d | d | d | d | d | d | d | c = compact pellet near the surface of the liquid, using magnetic separation
d = diffuse pellet at the bottom of the wells
n.d. = not done The average OD-signal and statistical values are given in Table 4. The OD value of the background signal determined in the wells without thioredoxin was on average 0.117 in wells with detergent and 0.109 in wells without detergent.

TABLE 4

|  | samples containing detergent | samples without detergent |
| --- | --- | --- |
| average OD value | 1.230 | 0.475 |
| standard deviation | 0.096 | 0.115 |
| CV-value | 7.8 | 24.3 |

Example 5

Effect of Different Detergents in Variable Concentrations on the Separation Behavior of Magnetic Agarose Beads Placed on a 96-Well Magnet This example describes the positive effects of a broad variety of detergents on the separation behaviour of magnetic beads.

A 20 µl sample of a 5% (v/v) suspension of magnetic agarose beads were diluted in 200 µl of distilled water. Concentrations of 1%, 0.5%, 0.1%, 0.05%, 0.01%, 0.005% and 0.0005% of detergents belonging to different classes were added, and separation behaviour of the magnetic beads was observed after placing the sample vessel (96-well plate) on a suitable magnetic separator (e.g., 96-Well Magnet, Qiagen GmbH, Product Guide 1999 Cat. No. 36915). Tween 20, Triton X-100 and Nonidet P-40 were tested as examples of nonionic detergents, sodium dodecylsulphate was tested as an anionic detergent, CHAPS was tested as a zwitterionic Sufficient concentrations of detergents for improved bead separation differed between the detergent classes. Whereas nonionic detergents could be reduced down to 0.0005% (v/v) to facilitate efficient bead separation, the anionic detergent was needed at 0.05% (v/v), the zwitterionic detergent was needed at 0.01% (v/v), and the cationic detergent was needed at 0.5% (v/v).

Example 6

Automated Immunoassay of 6x-His-Tagged Thioredoxin Using Ni-NTA Coated Magnetic Agarose Beads with Detergent Only in the First Buffer This example demonstrates that the addition of detergent only in the first step is sufficient to improve the uniformity of an automated protein assay procedure using magnetic agarose beads.

Purified 6x-His-tagged thioredoxin was diluted to 50 ng per 200 µl in dilution buffer (50 mM $NaH_2PO_4$, pH 8.0; 300 mM NaCl, 20 mM imidazole). 200 µl of the protein dilution was pipetted into each of 12 wells of a 96-well microplate. In addition, 200 µl of the same buffer without thioredoxin was added to 12 wells of the same 96-well microplate as a negative control. The multiwell plate was placed on the working platform of an automated pepetting system (BioRobot 9600, Qiagen GmbH) and 20 µl of a 2.5% (v/v) suspension of Ni-NTA-coated magnetic agaraose beads were dispensed into each well. The beads in protein-containing wells bound the 6x-His-tagged protein while incubating on a shaker platform at 750 rpm for 45 minutes at room temperature. Following the binding step, 0.1% Tween 20 nonionic detergent was added to 8 wells each. For all subsequent steps, 4 of the 8 wells were processed in the presence of 0.005% Tween 20, and the remaining 4 wells were processed in the absence of any detergent. The remaining 4 wells of each thioredoxin concentration were handled without detergent during the entire process. The plate was incubated for 15 minutes at room temperature and subsequently was transferred to a magnetic separator for 96-well plates as described above, and shaken for 2 minutes at 750 rpm to complete bead separation. Supernatant was aspirated and the plate was removed from the magnet. The magnetic beads were resuspended in 200 μl of wash buffer (50 mM NaH$_2$PO$_4$, pH 8.0; 300 mM NaCl, 20 mM imidazole, with and without 0.005% Tween 20), and the plate was shaken for 5 minutes at 750 rpm. The wash buffer was removed as before, and the beads were resuspended in 200 μl of binding buffer (50 mM NaH$_2$PO$_4$, pH 8.0; 300 mM NaCl, 3% BSA, with and without 0.005% Tween 20) containing a polyclonal antibody recognizing thioredoxin. As described above, some wells were incubated in the presence or absence of detergent. The plate was incubated on a shaker at room temperature for an hour at 750 rpm. The buffer was removed as described above and the beads were washed twice in wash buffer. Subsequently 200 μl of secondary antibody coupled to horseradish peroxidase, diluted in binding buffer +/−0.005% Tween 20 were added to each well and the plate was incubated on a shaker for an hour at room temperature at 750 rpm. The binding buffer was removed and the beads were washed four times with wash buffer. The amount of immobilized peroxidase was determined by the addition of 200 μl of color reagent (10 mg o-phenylene diamine in 25 ml sodium-phosphate buffer, pH 5.0; 25 μl H$_2$O$_2$). The plate was incubated at room temperature for 10 minutes and optical density was read at 450 nm.

The comparison of the three sets of wells that were processed in the presence or absence of detergent, or presence or absence of thioredoxin displayed differences in separation behavior of the magnetic beads. Beads in samples that received the detergent after the binding step were collected in a compact pellet near the surface of the liquid throughout the procedure, regardless of whether the detergent was added to the subsequent steps. In contrast, the samples in the absence of detergent during the binding step separated in diffuse pellets at the bottom of each well, which resulted in bead loss during the procedure. This bead loss resulted in lower signals and higher standard deviations between wells. In all the samples, the average OD value of the background signal was between 0.063 and 0.071. The statistical values of the amounts are shown in Table 6.

TABLE 6

Samples with addition of 0.1% detergent in the first step

|  | 0% detergent in all following steps | 0.005% detergent in all following steps | Samples without detergent throughout the entire procedure |
| --- | --- | --- | --- |
| Average value | 2.041 | 1.862 | 1.239 |
| Standard deviation | 0.110 | 0.056 | 0.488 |
| CV-value | 5.4% | 3.0% | 39.4% |

Standard protocols of molecular biology applications, enzymology, protein and nucleic acid chemistry are well described in printed publications such as *Molecular Cloning—A laboratory Manual*, Cold Spring Harbor, N.Y. (Sambrook et al. 1989); *PCR Protocols—A Guide to Methods and Applications*, Academic Press, N.Y. (Innis et al., eds, 1990), *PCR Primer—A Laboratory Manual*, CSHL Press (Dieffenbach and Dveksler, eds., 1995); and *Methods in Enzymology*, Academic Press, Inc.

All of the patents, patent applications, and publications cited herein are hereby incorporated by reference.

What is claimed is:

1. A method for isolating a fusion protein, wherein said fusion protein comprises a peptide, polypeptide, or protein and an affinity peptide tag consisting of a plurality of consecutive histidine residues from a sample in a vessel, comprising the steps of:
    (a) combining the sample containing the fusion protein with metal-chelate affinity particles suitable for binding said fusion protein, said metal-chelate affinity particles being insoluble in the sample;
    (b) collecting the metal-chelate affinity particles;
    (c) separating the metal-chelate affinity particles from the unbound remainder of the sample;
    (d) optionally, resuspending the metal-chelate affinity particles in a solution;
    (e) optionally, eluting said fusion protein from the metal-chelate affinity particles, followed by separating the metal-chelate affinity particles from said eluted fusion protein;

wherein at least one of steps (a), (b), (c), (d) if present, and (e) if present is performed in the presence of 0.0005%–2% (v/v) detergent sufficient to reduce loss of metal-chelate affinity particles during any separation or collection step, in comparison to the same method performed in the absence of detergent.

2. The method according to claim 1, wherein the combining step (a) is carried out in the absence of detergent, but detergent is added prior to the collecting step (b).

3. The method according to claim 1, wherein said affinity peptide tag is six consecutive histidine residues.

4. The method according to claim 1, wherein said metal-chelate affinity particles are selected from the group consisting of ferromagnetic beads, superparamagnetic beads, and combinations thereof.

5. The method according to claim 1, wherein said metal-chelate affinity particles are composed of materials selected from the group consisting of agarose, silica, nitrocellulose, cellulose, acrylamide, latex, polystyrene, polyacrylate, polymethacrylate, polyethylene polymers, glass particles, silicates, metal oxides, apatites, and combinations thereof.

6. The method according to claim 1, wherein said detergent is selected from a group consisting of nonionic detergents, anionic detergents, zwitterionic detergents, cationic detergents, and combinations thereof.

7. The method according to claim 6, wherein said nonionic detergent is selected from the group consisting of polyoxyethylene (10) cetyl alcohol, polyoxyethylene (20) cetyl alcohol, polyoxyethylene (23) lauryl alcohol, polyoxyethylene (4-5) p-t-octyl phenol, polyoxyethylene (7-8) p-t-octyl phenol, polyoxyethylene (9) p-t-octyl phenol, polyoxyethylene (9-10) p-t-octyl phenol, polyoxyethylene (9-10) nonylphenol, polyoxyehtylene (20) sorbitol monolaurate, polyoxyehtylene (20) sorbitol monopalmitate, polyoxyehtylene (20) sorbitol monooleate, octyl-β-glucoside, APO-10, APO-12, cyclohexyl-n-ethyl-β-D-maltoside, cyclohexyl-n-hexyl-β-D-maltoside, cyclohexyl-n-methyl-β-maltoside, n-decanoylsucrose, n-decyl-β-D-glucopyranoside, n-decyl-β-maltopyranoside, n-decyl-β-D-thiomaltoside, n-dodecanoyl sucrose, and heptane-1,2,3-triol, and combinations thereof.

8. The method according to claim 6, wherein said nonionic detergent is polyoxyethylene (20) sorbitol monolaurate at a concentration of at least about 0.005% (v/v).

9. The method according to claim 6, wherein said anionic detergent is selected from the group consisting of sodium dodecyl sulfate (SDS), sarkosyl, and combinations thereof.

10. The method claim 6, wherein said zwitterionic detergent is 3-[(cholamido-propyl)-dimethyl-ammonio]-1-propanesulfonate.

11. The method according to claim 6, wherein said cationic detergent dodecyl-trimethyl ammonium chloride.

12. The method according to claim 1, wherein the detergent, where present, is a nonionic detergent at a concentration of at least about 0.005% (v/v).

13. The method according to claim 1, wherein the detergent, where present, is a nonionic detergent at a concentration not exceeding about 2% (v/v).

14. The method according to claim 1, wherein the detergent, where present, is an anionic detergent at a concentration of at least about 0.05% (v/v).

15. The method according to claim 1, wherein the detergent, where present, is an anionic detergent at a concentration not exceeding about 1% (v/v).

16. The method according to claim 1, wherein the detergent, where present, is a cationic detergent at a concentration of at least about 0.5% (v/v).

17. The method according to claim 1, wherein the detergent, where present, is a cationic detergent at a concentration not exceeding about 1% (v/v).

18. The method according to claim 1, wherein the detergent, where present, is a zwitterionic detergent at a concentration of at least about 0.01% (v/v).

19. The method according to claim 1, wherein the detergent, where present, is a zwitterionic detergent at a concentration not exceeding about 2% (v/v).

20. A method for isolating a fusion protein, wherein said fusion protein comprises a peptide, polypeptide, or protein molecule and an affinity peptide tag consisting of a plurality of consecutive histidine residues from a sample in a vessel, comprising the steps of:

(a) providing a multiplicity of metal-chelate affinity particles and incubating said metal-chelate affinity particles in the presence of a detergent;

(b) combining the sample containing the fusion protein with metal-chelate affinity particles suitable for binding said fusion protein, said metal-chelate affinity particles being insoluble in the sample;

(c) collecting the metal-chelate affinity particles;

(d) separating the metal-chelate affinity particles from the unbound remainder of the sample;

(e) optionally, resuspending the metal-chelate affinity particles in a solution;

(f) optionally, eluting said fusion protein from the metal-chelate affinity particles, followed by separating the metal-chelate affinity particles from said eluted fusion protein;

wherein any of the steps (b), (c), (d), (e) if present, and (f) if present may optionally be also performed in the presence of 0.0005%–2% (v/v) detergent, wherein the use of detergent is sufficient to reduce loss of metal-chelate affinity particles during any separation or collection step, in comparison to the same method performed in the absence of detergent.

21. The method according to claim 20, wherein said affinity peptide tag is six consecutive histidine residues.

22. The method according to claim 20, wherein said metal-chelate affinity particles are selected from the group consisting of ferromagnetic beads, superparamagnetic beads, and combinations thereof.

23. The method according to claim 20, wherein said metal-chelate affinity particles are composed of materials selected from the group consisting of agarose, silica, nitrocellulose, cellulose, acrylamnide, latex, polystyrene, polyacrylate, polymethacrylate, polyethylene polymers, glass particles, silicates, metal oxides, apatites, and combinations thereof.

24. The method according to claim 20, wherein said detergent is selected from a group consisting of nonionic detergents, anionic detergents, zwitterionic detergents, cationic detergents, and combinations thereof.

25. The method according to claim 24, wherein said nonionic detergent is selected from the group consisting of polyoxyethylene (10) cetyl alcohol, polyoxyethylene (20) cetyl alcohol, polyoxyethylene (23) lauryl alcohol, polyoxyethylene (4-5) p-t-octyl phenol, polyoxyethylene (7-8) p-t-octyl phenol, polyoxyethylene (9) p-t-octyl phenol, polyoxyethylene (9-10) p-t-octyl phenol, polyoxyethylene (9-10) nonylphenol, polyoxyethylene (20) sorbitol monolaurate, polyoxyehtylene (20) sorbitol monopalmitate, polyoxyethylene (20) sorbitol monooleate, octyl-β-glucoside, APO-10, APO-12, cyclohexyl-n-ethyl-β-D-maltoside, cyclohexyl-n-hexyl-β-D-maltoside, cyclohexyl-n-methyl-β-maltoside, n-decanoylsucrose, n-decyl-β-D-glucopyranoside, n-decyl-β-maltopyranoside, n-decyl-β-D-thiomaltoside, n-dodecanoyl sucrose, and heptane-1,2,3-triol, and combinations thereof.

26. The method according to claim 25, wherein said nonionic detergent is polyoxyethylene (20) sorbitol monolaurate.

27. The method according to claim 24, wherein said anionic detergent is selected from the group consisting of sodium dodecyl sulfate (SDS), sarkosyl, and combinations thereof.

28. The method claim 24, wherein said zwitterionic detergent is 3-[(cholamido-propyl)-dimethyl-ammonio]-1-propanesulfonate.

29. The method according to claim 24, wherein said cationic detergent dodecyl-trimethyl ammonium chloride.

30. The method according to claim 20, wherein the detergent, where present, is a nonionic detergent at a concentration of at least about 0.005% (v/v).

31. The method according to claim 20, wherein the detergent, where present, is a nonionic detergent at a concentration not exceeding about 2% (v/v).

32. The method according to claim 20, wherein the detergent, where present, is an anionic detergent at a concentration of at least about 0.05% (v/v).

33. The method according to claim 20, wherein the detergent, where present, is an anionic detergent at a concentration not exceeding about 1% (v/v).

34. The method according to claim 20, wherein the detergent, where present, is a cationic detergent at a concentration of at least about 0.5% (v/v).

35. The method according to claim 20, wherein the detergent, where present, is a cationic detergent at a concentration not exceeding about 1% (v/v).

36. The method according to claim 20, wherein the detergent, where present, is a zwitterionic detergent at a concentration of at least about 0.01% (v/v).

37. The method according to claim 20, wherein the detergent, where present, is a zwitterionic detergent at a concentration not exceeding about 2% (v/v).

38. The method according to claim 20, wherein the molecule is a nucleic acid and the detergent is polyoxyethylene (20) sorbitol monolaurate at a concentration of at least about 0.005% (v/v).

39. The method according to claim 20, wherein the molecule is a protein or peptide and the detergent is polyoxyethylene (20) sorbitol monolaurate at a concentration of at least about 0.005% (v/v).

40. A method for isolating a fusion protein, wherein said fusion protein comprises a peptide, polypeptide, or protein molecule and an affinity peptide tag consisting of a plurality of consecutive histidine residues from a sample in a vessel, comprising the steps of:

(a) combining the sample containing the fusion protein with metal-chelate, magnetic affinity particles suitable for binding said fusion protein, said metal-chelate, magnetic affinity particles being insoluble in the sample;

(b) applying a magnetic field to the vessel so as to attract and immobilize the metal-chelate, magnetic affinity particles;

(c) separating the unimmobilized remainder of the sample from the immobilized metal-chelate, magnetic affinity particles;

(d) optionally, resuspending the metal-chelate, magnetic affinity particles in a solution;

(e) optionally, eluting said fusion protein from the metal-chelate, magnetic affinity particles, followed by separating the metal-chelate, magnetic affinity particles from said eluted fusion protein;

wherein at least one of steps (a), (b), (c), (d) if present, and (e) if present is performed in the presence of 0.0005%–2% (v/v) detergent sufficient to reduce loss of metal-chelate, magnetic affinity particles during any separation or collection step, in comparison to the same method performed in the absence of detergent.

41. The method according to claim 40, wherein the combining step (a) is carried out in the absence of detergent, but detergent is added prior to the application of a magnetic field in accordance with step (b).

42. A method for isolating a fusion protein comprising a peptide, polypeptide, or protein and an affinity peptide tag consisting of a plurality of consecutive histidine residues from a sample in a vessel, comprising the steps of:

(a) providing a multiplicity of metal-chelate, magnetic affinity particles and incubating said metal-chelate, magnetic affinity particles in the presence of a detergent;

(b) combining the sample containing the fusion protein with said metal-chelate, magnetic affinity particles suitable for binding said fusion protein, said metal-chelate, magnetic affinity particles being insoluble in the sample;

(c) immobilizing the metal-chelate, magnetic affinity particles by applying a magnet to said vessel;

(d) separating the remainder of the sample from the immobilized metal-chelate, magnetic affinity particles;

(e) optionally, resuspending the metal-chelate, magnetic affinity particles in a solution;

(f) optionally, eluting said fusion protein from the metal-chelate, magnetic affinity particles, followed by separating the metal-chelate, magnetic affinity particles from said eluted fusion protein;

wherein any of the steps (b), (c), (d), (e) if present, and (f) if present may optionally be also performed in the presence of 0.0005%–2% (v/v) detergent, wherein the use of detergent is sufficient to reduce loss of metal-chelate, magnetic, affinity particles during any separation or collection step, in comparison to the same method performed in the absence of detergent.

43. The method according to claim 5 or 23, wherein the polyethylene polymer is a polyvinyl alcohol.

44. The method according to claim 5 or 23, wherein the silicate is selected from the group consisting of calcium silicate, magnesium silicate, aluminum silicate, and combinations thereof.

45. The method according to claim 5 or 23, wherein the metal oxide is selected from the group consisting of titanium oxide, tin oxide, and combinations thereof.

46. The method for isolating a fusion protein according to any one of claims 40–42, wherein said fusion protein comprises a peptide, polypeptide, or protein and an affinity peptide tag consisting of six consecutive histidine residues and said metal-chelate, magnetic affinity particles are nickel-nitrilotriacetic acid agarose beads.

* * * * *